United States Patent
Hamad et al.

(10) Patent No.: US 10,124,294 B2
(45) Date of Patent: Nov. 13, 2018

(54) ON-BOARD FUEL ADJUSTMENT BY MOLECULAR SEPARATION

(71) Applicant: Saudi Arabian Oil Company, Dhahran (SA)

(72) Inventors: Esam Z. Hamad, Dhahran (SA); Christos M. Kalamaras, Al Khobar (SA)

(73) Assignee: Saudi Arabian Oil Company, Dhahran (SA)

( * ) Notice: Subject to any disclaimer, the term of this patent is extended or adjusted under 35 U.S.C. 154(b) by 239 days.

(21) Appl. No.: 15/190,639

(22) Filed: Jun. 23, 2016

(65) Prior Publication Data
US 2017/0368504 A1   Dec. 28, 2017

(51) Int. Cl.
*B01D 61/02* (2006.01)
*B01D 61/08* (2006.01)
(Continued)

(52) U.S. Cl.
CPC ........... *B01D 61/027* (2013.01); *B01D 61/08* (2013.01); *B01D 71/028* (2013.01); *B60K 15/03* (2013.01); *C07C 7/005* (2013.01); *C07C 7/144* (2013.01); *C10G 31/09* (2013.01); *C10L 1/04* (2013.01); *F02M 31/125* (2013.01);
(Continued)

(58) Field of Classification Search
CPC ...... B01D 61/027; B01D 61/08; C07C 7/005; C07C 7/144; F02M 37/0076; F02M 31/16
See application file for complete search history.

(56) References Cited

U.S. PATENT DOCUMENTS

| | | |
|---|---|---|
| 2,950,336 A | 8/1960 | Kimberlin, Jr. et al. |
| 6,972,093 B2 | 12/2005 | Partridge et al. |

(Continued)

FOREIGN PATENT DOCUMENTS

| | | |
|---|---|---|
| EP | 1443202 | 8/2004 |
| JP | 2010013948 | 1/2010 |

(Continued)

OTHER PUBLICATIONS

International Search Report and Written Opinion issued in International Application No. PCT/US2017/037130 dated Aug. 18, 2017; 14 pages.

*Primary Examiner* — Jacob Amick
(74) *Attorney, Agent, or Firm* — Fish & Richardson P.C.

(57) ABSTRACT

An on-board fuel separation system includes a supply fuel tank configured to store an input fuel stream; a fuel separator fluidly coupled to the supply fuel tank and configured to separate the input fuel stream into a first fractional fuel stream and a second fractional fuel stream. The fuel separator includes a membrane that includes a plurality of pores sized based on a molecular size of one or more components of the first fractional fuel stream. The system includes a first fractional fuel tank fluidly coupled to the fuel separator to receive the first fractional fuel stream passed through the membrane and defined by a first auto-ignition characteristic value. The system includes a second fractional fuel stream coupled to the fuel separator to receive the second fractional fuel stream from the fuel separator that is defined by a second auto-ignition characteristic value that is different than the first auto-ignition characteristic value.

23 Claims, 7 Drawing Sheets

(51) Int. Cl.
*C07C 7/00* (2006.01)
*C07C 7/144* (2006.01)
*F02M 31/16* (2006.01)
*C10G 31/09* (2006.01)
*C10L 1/04* (2006.01)
*F02M 37/00* (2006.01)
*B60K 15/03* (2006.01)
*F02M 37/22* (2006.01)
*F02M 31/125* (2006.01)
*F02M 31/18* (2006.01)
*B01D 71/02* (2006.01)
*F02M 37/04* (2006.01)
*F02D 19/06* (2006.01)

(52) U.S. Cl.
CPC ............ *F02M 31/16* (2013.01); *F02M 31/18* (2013.01); *F02M 37/0011* (2013.01); *F02M 37/0064* (2013.01); *F02M 37/0076* (2013.01); *F02M 37/0088* (2013.01); *F02M 37/223* (2013.01); *B01D 2311/103* (2013.01); *C10G 2300/1044* (2013.01); *C10G 2300/201* (2013.01); *C10G 2300/202* (2013.01); *C10G 2300/305* (2013.01); *C10G 2300/307* (2013.01); *C10L 2230/22* (2013.01); *C10L 2290/06* (2013.01); *C10L 2290/547* (2013.01); *C10L 2290/548* (2013.01); *F02D 19/06* (2013.01); *F02M 37/04* (2013.01); *Y02T 10/126* (2013.01)

(56) References Cited

U.S. PATENT DOCUMENTS

| 7,389,751 | B2 | 6/2008 | Leone |
| 7,426,907 | B2 | 9/2008 | Dearth et al. |
| 7,845,315 | B2 | 12/2010 | Leone et al. |
| 8,211,300 | B2 | 7/2012 | Partridge et al. |
| 8,550,058 | B2 | 10/2013 | Pursifull et al. |
| 8,580,111 | B2 | 11/2013 | Partridge et al. |
| 2002/0175109 | A1 | 11/2002 | Ragil et al. |
| 2003/0196931 | A1 | 10/2003 | Houzvicka et al. |
| 2005/0056264 | A1 | 3/2005 | Weissman et al. |
| 2006/0037589 | A1 | 2/2006 | Gupta et al. |
| 2010/0155315 | A1* | 6/2010 | Partridge ........... B01D 19/0031 210/149 |
| 2012/0132576 | A1* | 5/2012 | Partridge ............... B01D 61/36 210/175 |
| 2013/0168311 | A1 | 7/2013 | Johnson et al. |
| 2015/0059700 | A1 | 3/2015 | Leone et al. |

FOREIGN PATENT DOCUMENTS

| WO | WO2005/049181 | 6/2005 |
| WO | 2015/155813 | 10/2015 |

\* cited by examiner

FIG. 5

ON-BOARD FUEL ADJUSTMENT BY MOLECULAR SEPARATION

TECHNICAL FIELD

This disclosure relates to adjusting a fuel on-board a vehicle and, more particularly, dynamically separating fuel on-board according to at least one characteristic of the fuel.

BACKGROUND

Vehicles, such as cars, trucks, boats, all-terrain vehicles, and otherwise, typical use internal combustion engines for power. These engines require fuel, such as gasoline, diesel, or otherwise, to operate. The fuel is often characterized by an octane or cetane number.

SUMMARY

In a general implementation, a method for separating a fuel on-board a vehicle includes circulating an input fuel stream from a supply fuel tank on-board a vehicle to an on-board fuel separator to separate the input fuel stream into a first fractional fuel stream and a second fractional fuel stream, the on-board fuel separator including a membrane that includes a plurality of pores sized based on a molecular size of one or more components of the first fractional fuel stream, the membrane including a molecular sieve or nano-filter; passing the first fractional fuel stream through the membrane; and circulating the first and second fractional fuel streams to respective first and second fractional fuel tanks, the first fractional fuel stream defined by a first auto-ignition characteristic value, and the second fractional fuel stream defined by a second auto-ignition characteristic value that is different than the first auto-ignition characteristic value.

An aspect combinable with the general implementation further includes circulating the input fuel stream from the supply fuel tank to a heat exchanger fluidly coupled between the supply fuel tank and the on-board fuel separator; heating the input fuel stream in the heat exchanger; and circulating the heated input fuel stream to the on-board fuel separator.

An aspect combinable with any of the previous aspects further includes circulating at least one of the first or second fractional fuel streams to the heat exchanger; and transferring heat from the at least one first or second fractional fuel streams to the input fuel stream in the heat exchanger.

An aspect combinable with any of the previous aspects further includes reducing, based on the transferred heat, a temperature of the at least one first or second fractional fuel stream from at or near a vapor phase temperature to at or near a liquid phase temperature.

In another aspect combinable with any of the previous aspects, the heat exchanger includes a first heat exchanger.

In another aspect combinable with any of the previous aspects, circulating at least one of the first or second fractional fuel streams to the heat exchanger includes circulating the first fractional fuel stream to the first heat exchanger; transferring heat from the first fractional fuel stream to the input fuel stream; circulating the second fractional fuel stream to a second heat exchanger fluidly coupled to the first heat exchanger; and transferring heat from the second fractional fuel stream to the input fuel stream heated by the first fractional fuel stream in the first heat exchanger.

In another aspect combinable with any of the previous aspects, heating the input fuel stream in the heat exchanger includes heating the input fuel stream from a liquid phase temperature to at or near a vapor phase temperature.

An aspect combinable with any of the previous aspects further includes circulating the heated input fuel stream to a heater fluidly coupled between the heat exchanger and the on-board fuel separator; and heating the heated input fuel stream, with the heater, to at least the vapor phase temperature.

In another aspect combinable with any of the previous aspects, the first fractional fuel stream includes at least one of linear or mono-branch paraffins, and the second fractional fuel stream includes at least one of multi-branched paraffins, naphenes, aromatics, olefins, or oxygenates.

In another aspect combinable with any of the previous aspects, the first auto-ignition characteristic value includes a first research octane number (RON) or a first cetane number, and the second auto-ignition characteristic value includes a second RON or a second cetane number.

In another aspect combinable with any of the previous aspects, the first RON or cetane number is less than a RON or cetane number of the input fuel stream, and the second RON or cetane number is greater than the RON or cetane number of the input fuel stream.

In another aspect combinable with any of the previous aspects, the molecular size includes a molecular diameter.

In another general implementation, an on-board fuel separation system includes a supply fuel tank configured to store an input fuel stream; a fuel separator fluidly coupled to the supply fuel tank and configured to separate the input fuel stream into a first fractional fuel stream and a second fractional fuel stream, the fuel separator including a membrane that includes a plurality of pores sized based on a molecular size of one or more components of the first fractional fuel stream, the membrane including a molecular sieve or nanofilter; a first fractional fuel tank fluidly coupled to the fuel separator to receive the first fractional fuel stream passed through the membrane, the first fractional fuel stream defined by a first auto-ignition characteristic value; and a second fractional fuel stream coupled to the fuel separator to receive the second fractional fuel stream from the fuel separator, the second fractional fuel stream defined by a second auto-ignition characteristic value that is different than the first auto-ignition characteristic value.

An aspect combinable with the general implementation further includes a heat exchanger fluidly coupled to the supply fuel tank and configured to receive the input fuel stream from the supply fuel tank and heat the input fuel stream to deliver to the fuel separator.

In another aspect combinable with any of the previous aspects, the heat exchanger is fluidly coupled to the fuel separator to receive at least one of the first or second fractional fuel streams from the fuel separator to transfer heat, in the heat exchanger, from the at least one first or second fractional fuel streams to the input fuel stream.

In another aspect combinable with any of the previous aspects, a temperature of the at least one first or second fractional fuel stream is adjustable, in the heat exchanger, from at or near a vapor phase temperature to at or near a liquid phase temperature.

In another aspect combinable with any of the previous aspects, the heat exchanger includes a first heat exchanger and the system further includes a second heat exchanger.

In another aspect combinable with any of the previous aspects, the first fractional fuel stream is fluidly coupled from the fuel separator to the first heat exchanger to transfer heat from the first fractional fuel stream to the input fuel stream.

In another aspect combinable with any of the previous aspects, the second fractional fuel stream is fluidly coupled to from the fuel separator to the second heat exchanger to transfer heat from the second fraction fuel stream to the input fuel stream heated in the first heat exchanger.

In another aspect combinable with any of the previous aspects, the heat exchanger is configured to heat the input fuel stream from a liquid phase temperature to at or near a vapor phase temperature.

An aspect combinable with any of the previous aspects further includes a heater coupled between the heat exchanger and the fuel separator and configured to heat the heated input fuel stream to at least the vapor phase temperature.

In another aspect combinable with any of the previous aspects, the first fractional fuel stream includes at least one of linear or mono-branch paraffins.

In another aspect combinable with any of the previous aspects, the second fractional fuel stream includes at least one of multi-branched paraffins, naphenes, aromatics, olefins, or oxygenates.

In another aspect combinable with any of the previous aspects, the first auto-ignition characteristic value includes a first research octane number (RON) or a first cetane number.

In another aspect combinable with any of the previous aspects, the second auto-ignition characteristic value includes a second RON or a second cetane number.

In another aspect combinable with any of the previous aspects, the first RON or cetane number is less than a RON or cetane number of the input fuel stream, and the second RON or cetane number is greater than the RON or cetane number of the input fuel stream.

In another aspect combinable with any of the previous aspects, the molecular size includes a molecular diameter.

In another general implementation, a vehicle system includes a vehicle; a fuel-powered internal combustion engine mounted in the vehicle; a supply fuel tank; an on-board fuel separation system that includes a fuel separator fluidly coupled to the supply fuel tank and configured to separate an input fuel stream into a first fractional fuel stream and a second fractional fuel stream, the fuel separator including a membrane that includes a plurality of pores sized based on a molecular diameter of one or more components of the first fractional fuel stream, the membrane including a molecular sieve or nanofilter; a first fuel tank fluidly coupled to the fuel separator to receive the first fractional fuel stream passed through the membrane, the first fractional fuel stream defined by a first auto-ignition characteristic value; and a second fuel stream coupled to the fuel separator to receive the second fractional fuel stream from the fuel separator, the second fractional fuel stream defined by a second auto-ignition characteristic value that is different than the first auto-ignition characteristic value.

In an aspect combinable with the general implementation, the on-board fuel separation system further includes a heat exchanger fluidly coupled to the supply fuel tank and configured to receive the input fuel stream from the supply fuel tank and heat the input fuel stream.

In another aspect combinable with any of the previous aspects, the heat exchanger is fluidly coupled to the fuel separator to receive at least one of the first or second fractional fuel streams from the fuel separator to transfer heat, in the heat exchanger, from the at least one first or second fractional fuel streams to the input fuel stream.

In another aspect combinable with any of the previous aspects, a temperature of the at least one first or second fractional fuel stream is adjustable, in the heat exchanger, from at or near a vapor phase temperature to at or near a liquid phase temperature.

In another aspect combinable with any of the previous aspects, the heat exchanger includes a first heat exchanger and the system further includes a second heat exchanger.

In another aspect combinable with any of the previous aspects, the first fractional fuel stream is fluidly coupled from the fuel separator to the first heat exchanger to transfer heat from the first fractional fuel stream to the input fuel stream.

In another aspect combinable with any of the previous aspects, the second fractional fuel stream is fluidly coupled to from the fuel separator to the second heat exchanger to transfer heat from the second fraction fuel stream to the input fuel stream heated in the first heat exchanger.

In another aspect combinable with any of the previous aspects, the heat exchanger is configured to heat the input fuel stream from a liquid phase temperature to at or near a vapor phase temperature.

In another aspect combinable with any of the previous aspects, the on-board fuel separation system further includes a heater coupled between the heat exchanger and the fuel separator and configured to heat the heated input fuel stream to at least the vapor phase temperature.

In another aspect combinable with any of the previous aspects, the first fractional fuel stream includes at least one of linear or mono-branch paraffins, and the second fractional fuel stream includes at least one of multi-branched paraffins, naphenes, aromatics, olefins, or oxygenates.

In another aspect combinable with any of the previous aspects, the first auto-ignition characteristic value includes a first research octane number (RON) or a first cetane number, and the second auto-ignition characteristic value includes a second RON or a second cetane number.

In another aspect combinable with any of the previous aspects, the first RON or cetane number is less than a RON or cetane number of the input fuel stream, and the second RON or cetane number is greater than the RON or cetane number of the input fuel stream.

Implementations according to the present disclosure may include one or more of the following features. For example, implementations can reduce fuel consumption, fuel cost, as well as $CO_2$ emissions from vehicles. As another example, fuel consumption of a vehicle may be reduced by supplying the engine of the vehicle with a fuel that has an optimized auto-ignition characteristic value (for example, octane, cetane, or otherwise), rather than a higher volumetric flow rate of fuel. For instance, implementations may supply the engine with a fuel of a particular optimized auto-ignition characteristic value based on engine load or operating conditions. Such implementations may optimize the auto-ignition characteristic value of a single source of fuel stored on the vehicle (for example, in a fuel tank). Additionally, implementations described herein may optimize the auto-ignition characteristic value of fuel on-board the vehicle. As another example, implementations disclosed herein may provide for multiple fuel streams, each with different auto-ignition characteristic values, from a single fuel source stored on an operating vehicle. As yet another example, implementations may allow a vehicle driver to purchase a fuel with a low auto-ignition characteristic value (for example, low octane number), which is typically more cost-efficient, while still allowing the vehicle to use both the purchased fuel and a separated, higher value, fuel. As yet a further example, implementations may decrease the demand for high octane fuels which require complex processes in refineries that may potentially increase greenhouse gas emissions and fuels cost. As another example, implementations may separate a single fuel source on-board a vehicle into multiple fuel sources, each having a particular auto-ignition characteristic value, without requiring additional energy (for example, electricity or heat) for the separation process.

The details of one or more implementations of the subject matter described in this disclosure are set forth in the accompanying drawings and the description below. Other features, aspects, and advantages of the subject matter will become apparent from the description, the drawings, and the claims.

DETAILED DESCRIPTION

The present disclosure describes an on-board fuel separation system that may be mounted on-board a vehicle, such as a car, truck, boat, or other vehicle that utilizes an engine to generate motive power. In some aspects, the fuel separation system separates an input fuel stream into two or more fractional fuel streams based on relative differences in molecular size (for example, molecular weight, kinetic diameter, or other molecular dimension) between fractional components that compose the input fuel stream. The separated fractional components may each have different auto-ignition characteristic values (for example, RON, cetane number, or otherwise). In some aspects, the on-board fuel separation system may include a membrane fuel separator that includes a molecular sieve or nanofilter to separate the input fuel stream into fractional fuel streams based on the respective molecular size of components in the input fuel stream.

Figure 1:
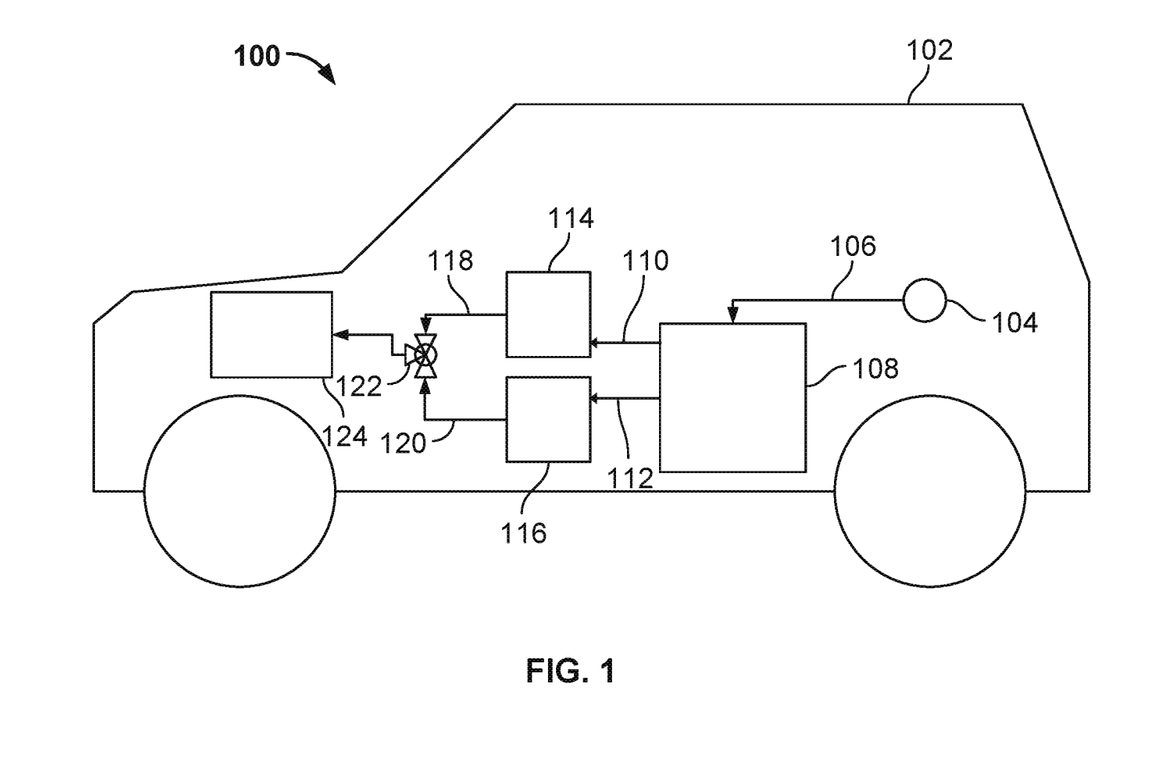
FIG. 1 is a schematic illustration of a multi-fuel vehicle system that includes an example implementation of an on-board fuel separation system according to the present disclosure.

FIG. 1 is a schematic illustration of a vehicle system 100 that includes an example implementation of an on-board fuel separation system 108 according to the present disclosure. As illustrated in FIG. 1, the vehicle system 100 includes a vehicle 100, which is represented as an automobile, but the present disclosure contemplates that a "vehicle" can include an automobile, motorized cycle, all-terrain vehicle (ATV), nautical vehicle (for example, boat or otherwise), or an airborne vehicle (for example, plane, ultralight, drone, or otherwise), whether manned or unmanned. Indeed, the present disclosure contemplates that a "vehicle" is any apparatus that derives powered movement from a hydrocarbon liquid fuel, such as gasoline, naphtha, or diesel as examples. A "vehicle" may also be any apparatus that includes an engine designed to use a fuel having an auto-ignition characteristic value, such as research octane number (RON) (or octane rating) (for example, in the case of gasoline fuels) or cetane number (for example, in the case of diesel fuels).

The illustrated vehicle 102 includes a fuel input 104 that is fluidly coupled to the on-board fuel separation system 108 to provide a fuel stream 106 to the separation system 108, for example, during operation of the vehicle 102. In some aspects, a fuel tank (not shown) is fluidly coupled in between the fuel input 104 and the on-board fuel separation system 108, for example, to contain a particular volume of fuel stream 106. In such aspects, the fuel stream 106 may be variably circulated (for example, pumped) from the fuel tank to the on-board fuel separation system 108, for example, as necessary for operation of the vehicle 102. In some aspects, a fuel rail of the vehicle could also be used for circulation of the fuel stream 106.

As described herein, the on-board fuel separation system 108 separates the fuel stream 106 into two or more individual fraction streams based on, for example, a particular characteristic of the fuel stream 106. For example, the fuel stream 106 may be separated into fractions based on relative molecular size of particular components, or fractional components, within the fuel stream 106. The fuel stream 106, in some aspects, may be separated into an aromatic or oxygenate fraction as well as other compound fractions (for example, linear and mono branch paraffins) based on the relative molecular size (for example, molecular diameter or otherwise).

For example, the on-board fuel separation system 108 separates the fuel stream 106 into two or more individual fraction streams based on the relative effective kinetic diameters of the particular fractional components of the fuel stream 106. As another example, the on-board fuel separation system 108 separates the fuel stream 106 into two or more individual fraction streams based on the relative effective molecular weight of the particular fractional components of the fuel stream 106. In some aspects, the on-board fuel separation system 108 may separate the input fuel stream 106 into a particular fractional fuel stream that includes linear or mono branch paraffins (or both) and another fractional fuel stream that includes one or more of highly branched paraffins, naphenes, aromatics, olefins, or oxygenates (or a combination thereof). In some aspects, the fractional fuel stream that includes linear or mono branch paraffins may have an auto-ignition characteristic value (for example, RON) that is less than an auto-ignition characteristic value (for example, RON) of the input fuel stream 106, while the fractional fuel stream that includes highly branched paraffins, naphenes, aromatics, olefins, or oxygenates may have an auto-ignition characteristic value (for example, RON) that is greater than an auto-ignition characteristic value (for example, RON) of the input fuel stream 106.

The illustrated vehicle 102 includes two or more fuel fraction conduits shown as 110 and 112, which fluidly couple the on-board fuel separation system 108 to fractional fuel tanks 114 and 116. For example, the fuel fraction conduit 110 may fluidly couple the on-board fuel separation system 108 to the fractional fuel tank 114 to store a fuel fraction output by the on-board fuel separation system 108 that has a particular auto-ignition characteristic value, while the fuel fraction conduit 112 may fluidly couple the on-board fuel separation system 108 to the fractional fuel tank 116 to store another fuel fraction output by the on-board fuel separation system 108 that has a different auto-ignition characteristic value. In particular implementations, the fractional fuel tank 114 may store a fuel fraction output by the on-board fuel separation system 108 that has a higher RON relative to a fuel fraction output by the on-board fuel separation system 108 that is stored in the fractional fuel tank 114. Although only two fractional fuel tanks are shown, the present disclosure contemplates that more than two fractional fuel tanks may be fluidly coupled to the on-board fuel separation system 108 (for example, depending on the number of fuel separators of the on-board fuel separation system 108).

In some aspects, the two fuel streams 118 and 120 may each be fed directly to the engine 124. For example, one fuel stream (of fuel streams 118 and 120) could by port-injected and the other fuel stream (of fuel streams 118 and 120) could be directly injected into the cylinders of the engine 124. This implementation may avoid any time lag in providing the correct fuel to the engine 124, as a time lag could result from the fuel already in the fuel line after valve 122. In some aspects, the fuel route for the fuel streams 118 and 120 is kept as short as possible.

In this example schematic illustration, the fractional fuel tanks 114 and 116 are fluidly coupled to an engine 124 (for example, internal combustion gasoline, naphtha, or diesel engine) through fractional fuel supply lines 118 and 120 and a control valve 122. For example, the fractional fuel tank 114 (for example, which stores a higher RON fuel fraction) is fluidly coupled to the engine 124 through the supply line 118, while the fractional fuel tank 116 (for example, which stores a lower RON fuel fraction) is fluidly coupled to the engine 124 through the supply line 120. Based on, for example, dynamic (for example, instantaneous or real-time) driving conditions, such as speed vs. torque conditions, the control valve 122 may be controlled (for example, by a vehicle control system, not shown) to supply a particular fuel fraction stored in one of the fractional fuel tanks 114/116 to the engine 124. The supplied fuel fraction may have an auto-ignition characteristic value (for example, RON or cetane number) optimized for the dynamic (for example, instantaneous or real-time) driving conditions. For example, a higher RON fuel fraction (for example, stored in tank 114) may be circulated to the engine 124 based on high load engine conditions, high speed engine conditions, or a combination thereof. A lower RON fuel fraction (for example, stored in tank 116) may be circulated to the engine 124 based on low load engine conditions, low speed engine conditions, or a combination thereof.

In some aspects, the on-board fuel separation system 108 may help reduce fuel consumption, cost and $CO_2$ emissions. For example, depending on engine operating requirements (for example, dynamic or in real-time), a fuel fraction that has minimum required auto-ignition characteristic value (for example, RON) is supplied to the engine 124 (and not more as is conventional). Therefore, the on-board fuel separation system 108 may store a relatively high RON fuel fraction (for example, in fractional fuel tank 114) for the high load and high speed operating conditions. Similarly, a relatively low RON fuel fraction is stored (for example, in fractional fuel tank 116) for low load and low speed operating conditions.

In some aspects, the fractional fuel tanks 114 and 116 may be eliminated from the system 100, and, thus, one of the fuel fractions (for example, a higher RON fraction or lower RON fraction) may be circulated in real-time (for example, during operation of the engine 124 to power the vehicle 102) from the on-board fuel separation system 108 to the engine 124 as dictated by the engine operating conditions (for example, speed vs. torque, engine map operating point, or otherwise). Thus, in some aspects, the only fuel storage tank on the vehicle 102 may be fluidly coupled between the fuel input 104 and the on-board fuel separation system 108 (for example, a standard vehicle fuel tank). Therefore, in some aspects, the on-board fuel separation system 108 may be integrated into a conventional vehicle 102 that includes a single fuel tank.

Figure 2:
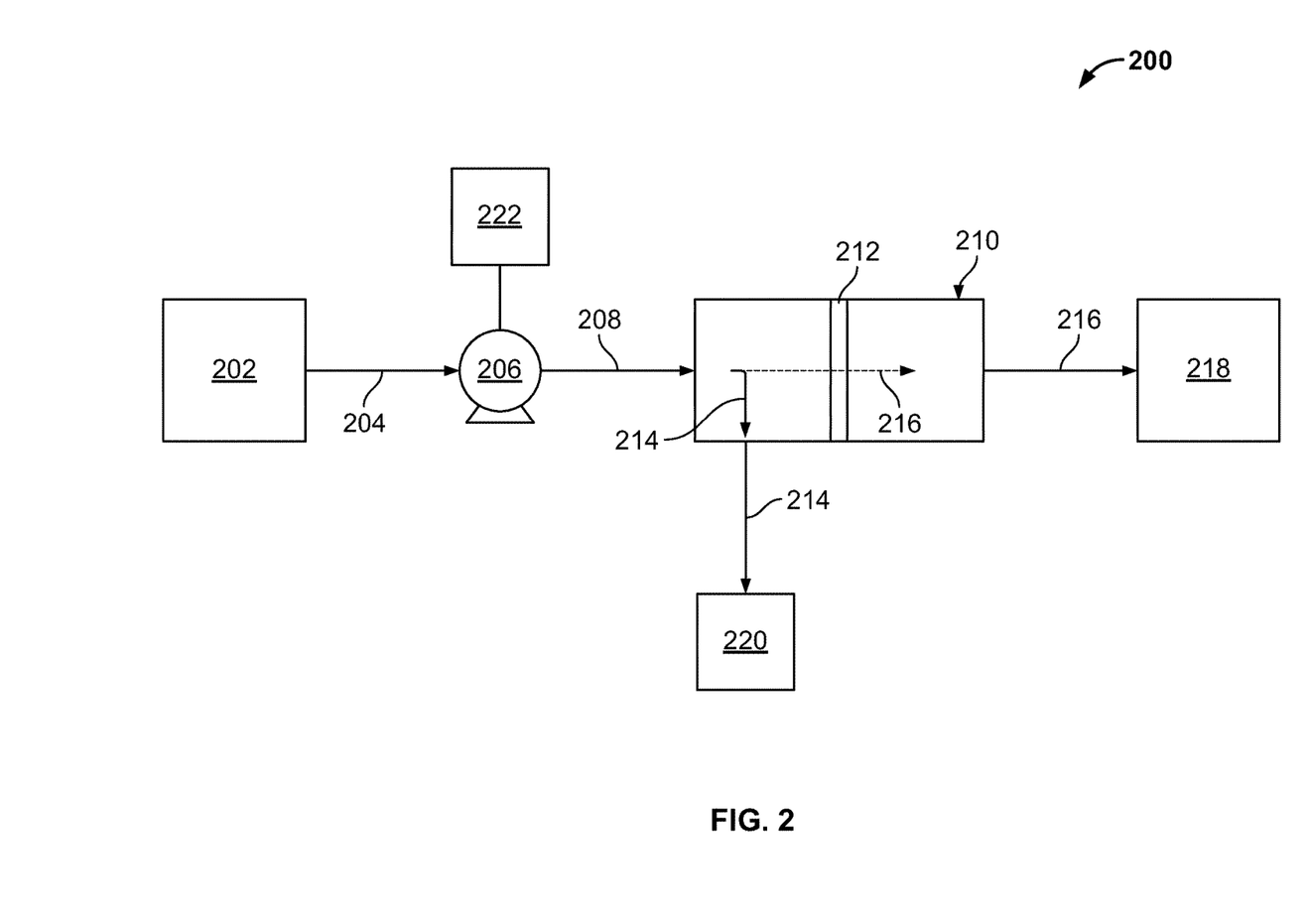
FIG. 2 is a schematic illustration of an example implementation of an on-board fuel separation system according to the present disclosure.

FIG. 2 is a schematic illustration of an example implementation of an on-board fuel separation system 200 according to the present disclosure. In some aspects, at least a portion of the system 200 may be implemented as the on-board fuel separation system 108 in the vehicle 102 shown in FIG. 1. In some aspects, the implementation of the on-board fuel separation system 200 shown in FIG. 2 implements a process for separating a liquid input fuel stream into liquid fractional component fuel streams based on relative differences in molecular size (for example, kinetic diameter, molecular weight, or otherwise) in the components of the input fuel stream.

As illustrated, the on-board fuel separation system 200 includes an input fuel tank 202 that stores an input fuel supply, such as the input fuel 106. The input fuel supply can be, for example, gasoline (for example, gasoline with a 91 RON, gasoline with a 95 RON, gasoline with another RON, light straight-run naphtha (LSRN), diesel, or another fuel supply for an internal combustion engine).

A pump 206 is fluidly coupled to the supply fuel tank 202 to circulate an input fuel stream 204 from the tank 202 (for example, upon a call for movement of a vehicle). The pump 206, in some aspects, may be part of a vehicle fuel rail or may be an additional pump that is part of a vehicle. The input fuel stream 204 is pressurized by the pump 206 and circulated as a pressurized fuel stream 208 to a fuel separator 210.

The fuel separator 210, in this example implementation, includes a membrane 212 that is composed of a plurality of pores. For example, in some aspects, the membrane 212 may be a molecular sieve (made from polymers or inorganic material) that separates the pressurized input fuel stream 208 into a retentate liquid fuel stream 214 and a permeate liquid fuel stream 216. For instance, the permeate liquid fuel stream 216 may be composed of fractional components of the pressurized fuel stream 208 that are sized (for example, by their kinetic diameter) to fit through the pores of the membrane 212. The retentate liquid fuel stream 214 may be composed of fractional components of the pressurized fuel stream 208 that are too large for (for example, have a kinetic diameter that exceeds a size of) the pores in the membrane 212.

The illustrated membrane 212 may, alternatively, be a nanofilter that separates the pressurized input fuel stream 208 into the retentate liquid fuel stream 214 and the permeate liquid fuel stream 216 based on a relative difference in molecular weight of the components in liquid streams 214 and 216. The retentate liquid fuel stream 214 may be composed of fractional components of the pressurized fuel stream 208 that are too large for (for example, have a molecular weight that exceeds a size of) the pores in the membrane 212, while the permeate liquid fuel stream 216 may be composed of fractional components of the pressurized fuel stream 208 that are sized (for example, by their molecular weight) to fit through the pores of the membrane 212.

The membrane 212 may be composed of organic (for example, polymeric) material, or inorganic material, such as a ceramic material. The membrane 212 may be composed of a structure that is composite or a simple membrane, porous or nonporous. The membrane 212 could be cast as, for example, a hollow fiber or a spiral wound or flat sheet, as long as the flux and module size is practical for on-board use in the on-board fuel separation system 200. For separating gasoline or naphtha, the membrane 212 may possess pores size in the range of from 4 to 8 angstroms (Å). In some aspects, the pores size is in the range from 4.5 to 6 Å.

The separated components of the permeate liquid fuel stream 216 and the retentate liquid fuel stream 214 may, due at least in part to their respective compositions, have different auto-ignition characteristic values (for example, different RON or cetane numbers). For example, in some implementations of system 200, the permeate liquid fuel stream 216 may have a lower RON (or cetane number) than a RON (or cetane number) of the pressurized liquid fuel stream 208. The retentate liquid fuel stream 214 may have a higher RON (or cetane number) than the RON (or cetane number) of the pressurized liquid fuel stream 208, as well as the RON (or cetane number) of the permeate liquid fuel stream 216.

In a specific example of system 200, the pressurized fuel stream 208 may be separated into the permeate liquid fuel stream 216 that includes linear or mono branch paraffins, or both. The retentate liquid fuel stream 214 may be composed of highly branched paraffins, naphenes, aromatics, olefins, oxygenates, or a combination thereof.

As shown in FIG. 2, the permeate liquid fuel stream 216 is directed to a permeate fractional fuel tank 218, to be stored for later or on-demand use in an engine. The retentate liquid fuel stream 214 is directed to a retentate fractional fuel tank 220, to also be stored for later or on-demand use in the engine. For example, based on instantaneous or real-time driving conditions, the engine may perform optimally with the retentate liquid fuel stream 214. Alternatively, based on different driving conditions of the vehicle, the engine may perform optimally with the permeate liquid fuel stream 216.

As illustrated, the on-board fuel separation system 200 includes a control system 222 that is communicably coupled one or more components of the on-board fuel separation system 200, for example, the pump 206 or other components (for example, valves, pumps, and other components, not shown). In some aspects, the control system 222 may be a mechanical, pneumatic, electro-mechanical, or micro-processor based control system (or a combination thereof). The control system 222 may receive (or store) inputs associated with engine operating characteristics of an engine of a vehicle that includes the on-board fuel separation system 200 and, based on the received (or stored) inputs, send control signals to, for example, the pump 206, one or more valves that adjust or control the temperature, the flow rates of the fuel streams 204, 208, 216, and 214, or a combination thereof. The control system 212 may also be communicably coupled to the separator 210 to control, for example, operating temperature, pressure, or pressures, of the separator 210.

The ability for the engine to select between fuel sources with different RON or cetane values may be beneficial. For example, in some implementations, at high load, gasoline engines require high octane (for example, long ignition delay) fuel to avoid knocking and engine damage. In some aspects, the on-board controller 222 may have an estimate of the amount of the high RON fuel (and associated RON value) based on a factory setting, driving history, or both. For instance, the controller 222 may control the circulation of the high RON fuel (for example, the retentate liquid fuel stream 214) or a low RON fuel (for example, the permeate liquid fuel stream 216) to the engine based on a predetermined or specified vapor-liquid ratio, vapor lock index, drivability index, or a combination thereof, for gasoline fuels. The controller 222 may control the circulation of the high RON fuel (for example, the retentate liquid fuel stream 214) or the low RON fuel (for example, the permeate liquid fuel stream 216) to the engine based on a predetermined or specified T90 or T95, lubricity, viscosity, or a combination thereof, for diesel fuels.

The controller 222 may also have predictive functions that give the RON and flow values at each operating pressure or temperature of the separator 210, the fuel specifications (for example, vapor lock index, T95, and other specifications), or otherwise. The controller 222 may then set the separator 222 pressure or temperature or other operating characteristics, to particular values to maximize the amount of the high RON fuel.

In an example operation of the system 200, the pump 206 pressurizes the input fuel stream 204 from the supply fuel tank 202 and circulates the pressurized input fuel stream 208 to the fuel separator 210. Based on, for example, an operating pressure of the fuel separator 210, the pressurized fuel stream 208 is separated by the membrane 212 into the permeate liquid fuel stream 216 and the retentate liquid fuel stream 214. For example, at a particular operating pressure of the fuel separator 210, certain components of the pressurized liquid fuel stream 208 (for example, linear and mono branch paraffins) permeate through the membrane 212 while other components (for example, highly branched paraffins, naphenes, aromatics, olefins and oxygenates) remain in the retentate liquid fuel stream 214. The membrane 212 separates the permeate components and the retentate components based on, for example, a kinetic diameter, a molecular weight, or other molecular dimensions of such components. The pump 206 (or other fluid circulation device) circulates the permeate liquid fuel stream 216 to the permeate fuel tank 218 and the retentate liquid fuel stream 214 to the retentate fuel tank 220.

Figure 3:
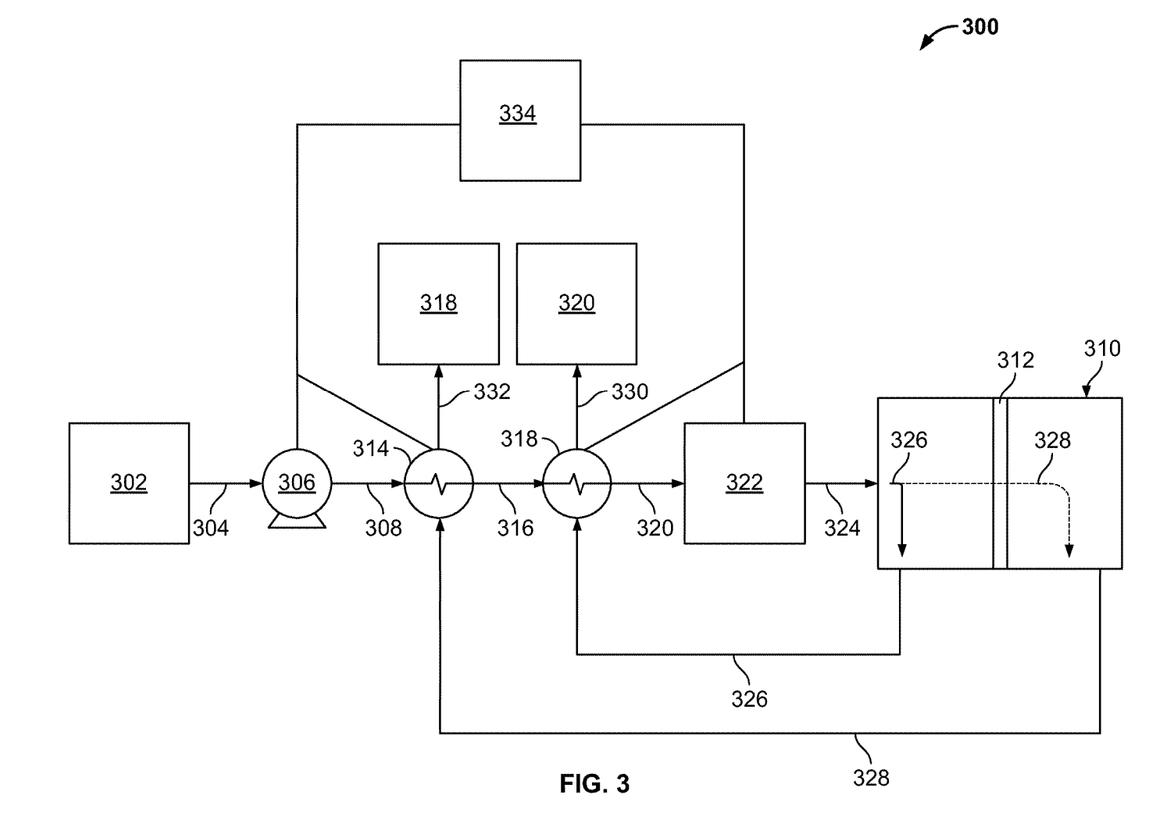
FIG. 3 is a schematic illustration of another example implementation of an on-board fuel separation system according to the present disclosure.

FIG. 3 is a schematic illustration of another example implementation of an on-board fuel separation system 300 according to the present disclosure. In some aspects, at least a portion of the system 300 may be implemented as the on-board fuel separation system 108 in the vehicle 102 shown in FIG. 1. In some aspects, the implementation of the on-board fuel separation system 300 shown in FIG. 3 implements a process for separating a vapor (or mixed phase) input fuel stream into vapor (or mixed phase) fractional component fuel streams based on relative differences in molecular size (for example, kinetic diameter, molecular weight, or otherwise) in the components of the input fuel stream. The separated vapor fuel streams may then be cooled (for example, condensed) into liquid fuel streams for use by an engine of a vehicle.

As illustrated, the on-board fuel separation system 300 includes an input fuel tank 302 that stores an input fuel supply, such as the input fuel 106. The input fuel supply can be, for example, gasoline (for example, gasoline with a 91 RON, gasoline with a 95 RON, gasoline with another RON, light straight-run naphtha (LSRN), diesel, or another fuel supply for an internal combustion engine).

A pump 306 is fluidly coupled to the supply fuel tank 302 to circulate an input fuel stream 304 from the tank 302 (for example, upon a call for movement of a vehicle). The pump 306, in some aspects, may be part of a vehicle fuel rail or may be an additional pump that is part of a vehicle. The input fuel stream 304 is pressurized by the pump 306 and circulated as a pressurized fuel stream 308 to a heat exchanger 314.

The heat exchanger 314 receives the pressurized input fuel 308 and a permeate fuel stream 328 from a fuel separator 310. The heat exchanger 314 (for example, a plate and frame, shell and tube, fin and tube, or other form of heat exchanger) transfers heat from the permeate fuel stream 328 to the pressurized input fuel stream 308, which exits the heat exchanger 314 as a heated pressurized input fuel stream 316. In some aspects, the pressurized input fuel stream 308 is liquid or mostly liquid (for example, a mixed phase mostly liquid fluid). The permeate fuel stream 328 may be vapor or mostly vapor (for example, a mixed phase mostly vapor fluid). Heating the pressurized input fuel stream 308 with the permeate fuel stream 328, in some aspects, may raise a temperature of the pressurized input fuel stream 308 to at or near a vapor temperature, thereby vaporizing all or a part of the pressurized fuel stream 308. The permeate fuel stream 328 may cool to a temperature at or near a liquid temperature, thereby condensing all or a part of the permeate fuel stream 308 in the heat exchanger 314.

The heat exchanger 314 is fluidly coupled, in this example implementation, to another heat exchanger 318. The heat exchanger 318 receives the heated pressurized input fuel 316 and a retentate fuel stream 326 from the fuel separator 310. The heat exchanger 318 (for example, a plate and frame, shell and tube, fin and tube, or other form of heat exchanger) transfers heat from the retentate fuel stream 326 to the heated pressurized input fuel stream 316, which exits the heat exchanger 318 as a pressurized vapor input fuel stream 320. In some aspects, the heated pressurized input fuel stream 316 is not fully vapor (for example, a mixed phase mostly vapor fluid). The retentate fuel stream 326 may be vapor or mostly vapor (for example, a mixed phase mostly vapor fluid). Further heating the heated pressurized input fuel stream 316 with the retentate fuel stream 326, in some aspects, may raise a temperature of the heated pressurized input fuel stream 316 to at or above the vapor temperature, thereby vaporizing all of the heated pressurized fuel stream 316. The retentate fuel stream 326 may cool to a temperature at or near a liquid temperature, thereby condensing all or a part of the retentate fuel stream 326 in the heat exchanger 318.

In some examples, the heat exchangers 314 and 318 may be combined into a single heat exchanger that receives, in one portion (for example, a portion of tubes or channels), the permeate fuel stream 328 and, in another portion (for example, another portion of tubes or channels), the retentate fuel stream 326. Thus, the pressurized input fuel stream 308 may be circulated through a single heat exchanger to receive heat from both the permeate fuel stream 328 and the retentate fuel stream 326.

As illustrated, the system 300 includes a heater 322 that is fluidly coupled between the heat exchanger 318 and the fuel separator and receives the pressurized vapor input fuel stream 320 from the heat exchanger 318. In some example implementations, the heater 322 may be an electric heater (for example, electric resistance heater) or may be a mechanical heat exchanger (for example, plate and frame, shell and tube, fin and tube, or otherwise). For example, as a mechanical heat exchanger, a heated fluid (for example, engine exhaust, vehicle coolant, or otherwise) may be circulated to the heater 322 to further transfer heat to the pressurized vapor input fuel stream 320. In some aspects, for example, the heater 322 may be controlled (for example, by a control system or controller 334) to add heat, if necessary, to ensure that the vaporized input fuel stream 320 (which exits the heater 322 as stream 324) is fully vaporized, superheated, or otherwise, to ensure a desired separation of fuel components in the fuel separator 310.

The fuel separator 310 is fluidly coupled, in this example implementation, to the heater 322 to receive the vaporized input fuel stream 324. The fuel separator 310 includes a membrane 312 that is composed of a plurality of pores. For example, in some aspects, the membrane 312 may be a molecular sieve that separates the vaporized input fuel stream 324 into the retentate liquid fuel stream 326 and the permeate liquid fuel stream 328. For instance, the permeate fuel stream 328 may be composed of fractional components of the vaporized input fuel stream 324 that are sized (for example, by their kinetic diameter) to fit through the pores of the membrane 312. The retentate fuel stream 326 may be composed of fractional components of the vaporized input fuel stream 324 that are too large for (for example, have a kinetic diameter that exceeds a size of) the pores in the membrane 312.

The illustrated membrane 312 may, alternatively, be a nanofilter that separates the vaporized input fuel stream 324 into the retentate fuel stream 326 and the permeate fuel stream 328 based on a relative difference in molecular weight of the components in liquid streams 326 and 328. The retentate fuel stream 326 may be composed of fractional components of the vaporized input fuel stream 324 that are too large for (for example, have a molecular weight that exceeds a size of) the pores in the membrane 312, while the permeate fuel stream 328 may be composed of fractional components of the vaporized input fuel stream 324 that are sized (for example, by their molecular weight) to fit through the pores of the membrane 312.

The membrane 312 may be composed of organic (for example, polymeric) material, or inorganic material, such as a ceramic material. The membrane 312 may be composed of a structure that is composite or a simple membrane, porous or nonporous. The membrane 312 could be cast as, for example, a hollow fiber or a spiral wound or flat sheet, as long as the flux and module size is practical for on-board use in the on-board fuel separation system 300. For separating gasoline or naphtha, the membrane 312 may possess a pore size in the range of from 4 to 8 Å. In some aspects, the pore size is in the range from 4.5 to 6 Å.

The separated components of the permeate fuel stream 328 and the retentate fuel stream 326 may, due at least in part to their respective compositions, have different auto-ignition characteristic values (for example, different RON or cetane numbers). For example, in some implementations of system 300, the permeate fuel stream 328 may have a lower RON (or cetane number) than a RON (or cetane number) of the input fuel stream 304. The retentate fuel stream 326 may have a higher RON (or cetane number) than the RON (or cetane number) of the input fuel stream 304, as well as the RON (or cetane number) of the permeate fuel stream 328.

In a specific example of system 300, the vaporized input fuel stream 324 may be separated into the permeate fuel stream 328 that includes linear or mono branch paraffins, or both. The retentate fuel stream 326 may be composed of highly branched paraffins, naphenes, aromatics, olefins, oxygenates, or a combination thereof.

As shown in FIG. 3, a permeate liquid or mostly liquid fuel stream 332 is directed to a permeate fractional fuel tank 318 after passing through the heat exchanger 314, to be stored for later or on-demand use in an engine. A retentate liquid or mostly liquid fuel stream 330 is directed to a retentate fractional fuel tank 320, to also be stored for later or on-demand use in the engine. For example, based on instantaneous or real-time driving conditions, the engine may perform optimally with the retentate liquid or mostly liquid fuel stream 330. Alternatively, based on different driving conditions of the vehicle, the engine may perform optimally with the permeate liquid or mostly liquid fuel stream 332.

As illustrated, the on-board fuel separation system 300 includes a control system 334 that is communicably coupled one or more components of the on-board fuel separation system 300, for example, the pump 306, heat exchangers 314/318, heater 322, or other components (for example, valves, pumps, and other components, not shown). In some aspects, the control system 334 may be a mechanical, pneumatic, electro-mechanical, or micro-processor based control system (or a combination thereof). The control system 334 may receive (or store) inputs associated with engine operating characteristics of an engine of a vehicle that includes the on-board fuel separation system 300 and, based on the received (or stored) inputs, send control signals to, for example, the pump 306, one or more valves that adjust or control the temperature, the flow rates of the fuel streams 304, 308, 316, 320, 324, or a combination thereof. The control system 334 may also be communicably coupled to the separator 310 to control, for example, operating temperature, pressure, or pressures, of the separator 310.

The ability for the engine to select between fuel sources with different RON or cetane values may be beneficial. For example, in some implementations, at high load, gasoline engines require high octane (for example, long ignition delay) fuel to avoid knocking and engine damage. In some aspects, the on-board controller 334 may have an estimate of the amount of the high RON fuel (and associated RON value) based on a factory setting, driving history, or both. For instance, the controller 334 may control the circulation of the high RON fuel (for example, the retentate liquid fuel stream 330) or a low RON fuel (for example, the permeate liquid fuel stream 332) to the engine based on a predetermined or specified vapor-liquid ratio, vapor lock index, drivability index, or a combination thereof, for gasoline fuels. The controller 334 may control the circulation of the high RON fuel (for example, the retentate liquid fuel stream 330) or the low RON fuel (for example, the permeate liquid fuel stream 332) to the engine based on a predetermined or specified T90 or T95, lubricity, viscosity, or a combination thereof, for diesel fuels.

The controller 334 may also have predictive functions that give the RON and flow values at each operating pressure or temperature of the separator 310, the fuel specifications (for example, vapor lock index, T95, and other specifications), or otherwise. The controller 334 may then set the separator 334 pressure or temperature or other operating characteristics, to particular values to maximize the amount of the high RON fuel.

In an example operation of the system 300, the pump 306 pressurizes the input fuel stream 304 from the supply fuel tank 302 and circulates the pressurized input fuel stream 308 to the heat exchanger 314. The pressurized fuel stream 308 is heated in the heat exchanger 314 with heat from the permeate fuel stream 328 (for example, in vapor form) and output from the heat exchanger 314 as the heated pressurized input fuel 316. The heated pressurized input fuel 316 may be at or near a vapor temperature of the input fuel 304 and is circulated to the heat exchanger 318. The heated pressurized fuel stream 316 is heated in the heat exchanger 318 with heat from the retentate fuel stream 326 (for example, in vapor form) and output from the heat exchanger 318 as the vaporized (or near vaporized) input fuel stream 320. The vaporized (or near vaporized) input fuel stream 320 is circulated to the heater 322, where the stream 320 is vaporized, if necessary.

The vaporized input fuel stream 324 is circulated to the fuel separator 310. Based on, for example, an operating pressure of the fuel separator 310, the vaporized input fuel stream 324 is separated by the membrane 312 into the permeate vapor fuel stream 328 and the retentate vapor fuel stream 326. For example, at a particular operating pressure of the fuel separator 310, certain components of the vaporized input fuel stream 324 (for example, linear and mono branch paraffins) permeate through the membrane 312 while other components (for example, highly branched paraffins, naphenes, aromatics, olefins and oxygenates) remain in the retentate vapor fuel stream 326. The membrane 312 separates the permeate components and the retentate components based on, for example, a kinetic diameter, a molecular weight, or other molecular dimension of such components.

The pump 306 (or other fluid circulation device) circulates the permeate vapor fuel stream 328 to the heat exchanger 314, where the stream 328 condenses to the permeate liquid fuel stream 332 to be stored in the permeate fuel tank 318. Further, the pump 306 (or other fluid circulation device) circulates the retentate vapor fuel stream 326 to the heat exchanger 318, where the stream 326 condenses to the retentate liquid fuel stream 330 to be stored in the retentate fuel tank 320.

Figure 4A:
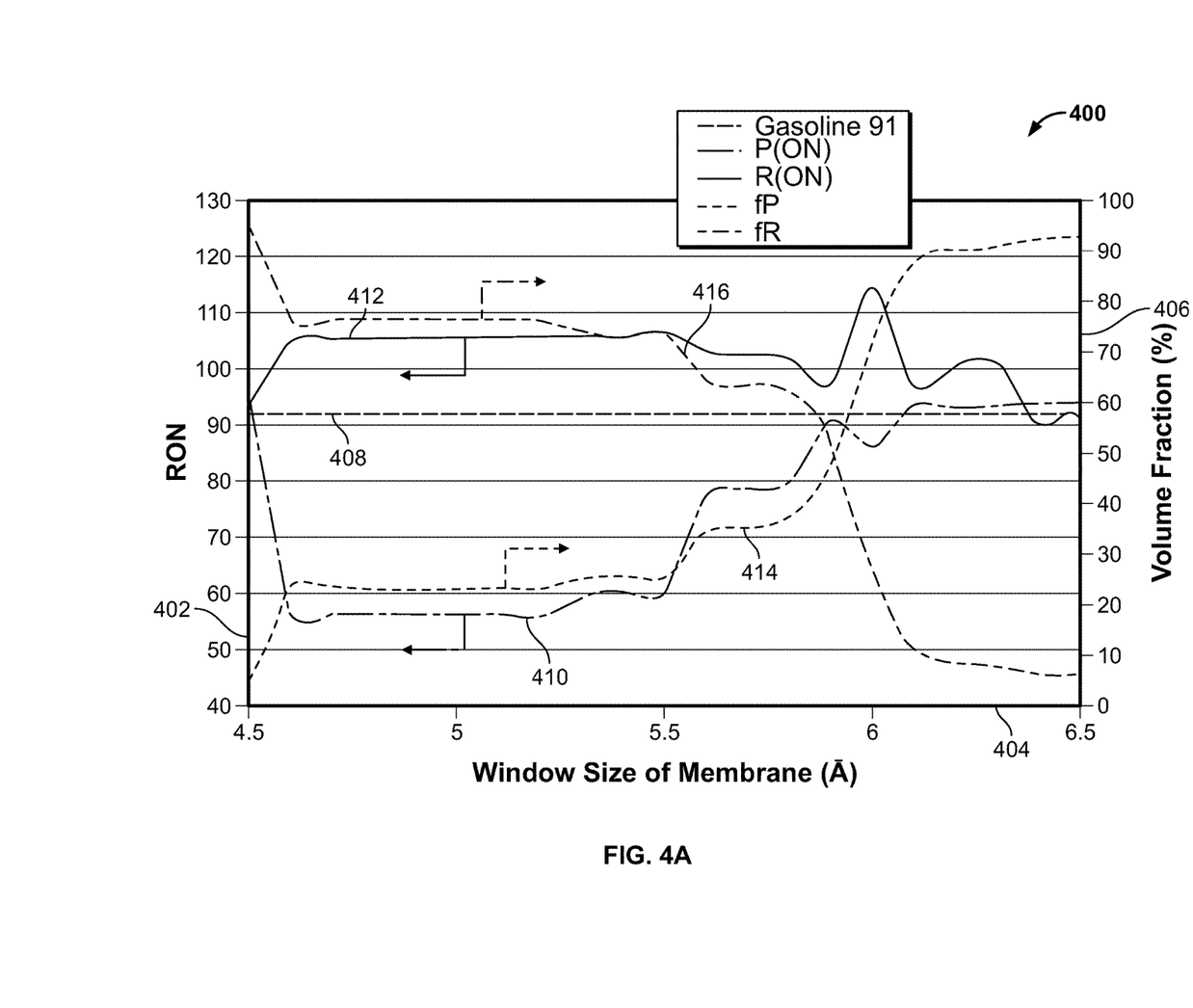
FIGS. 4A-4C are graphs that illustrate results of a simulation model of an on-board fuel separation system according to the present disclosure.
Figure 4B:
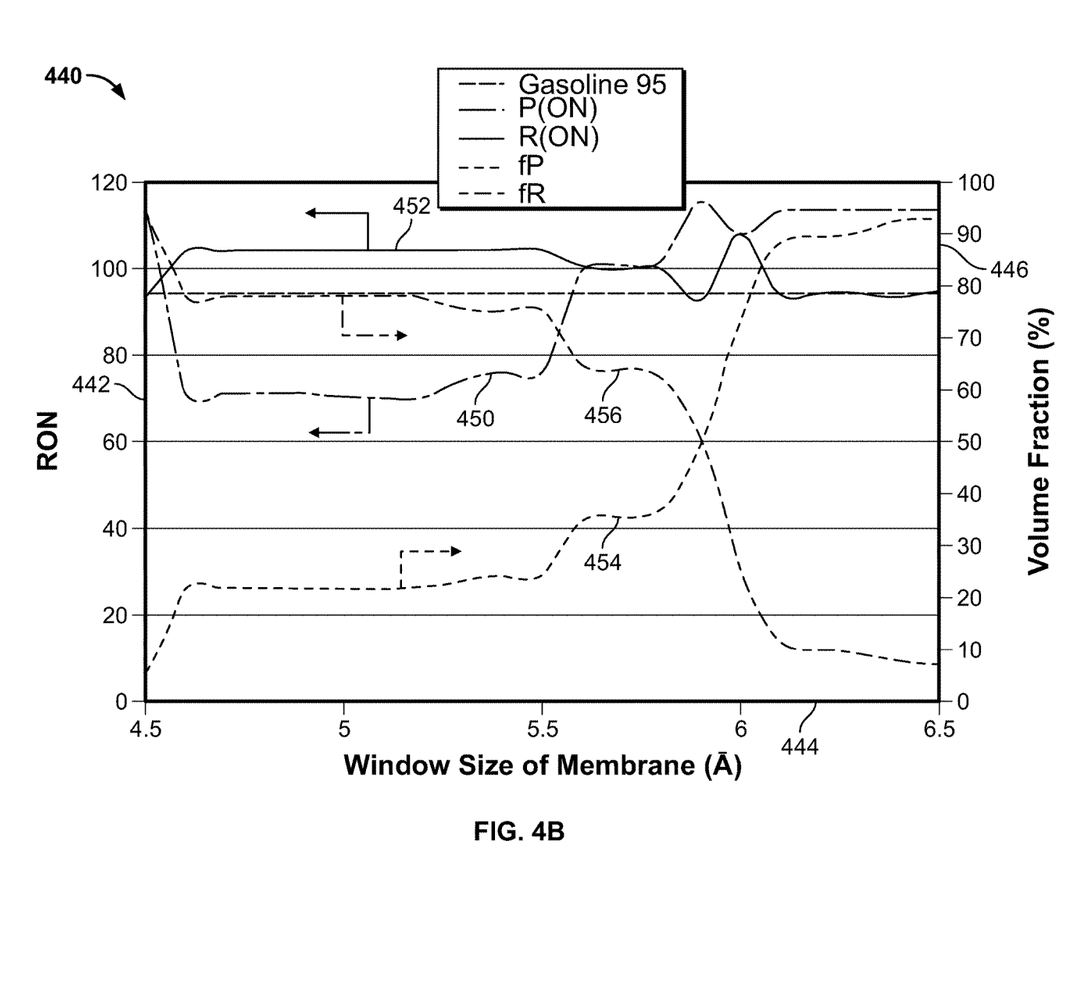
Figure 4C:
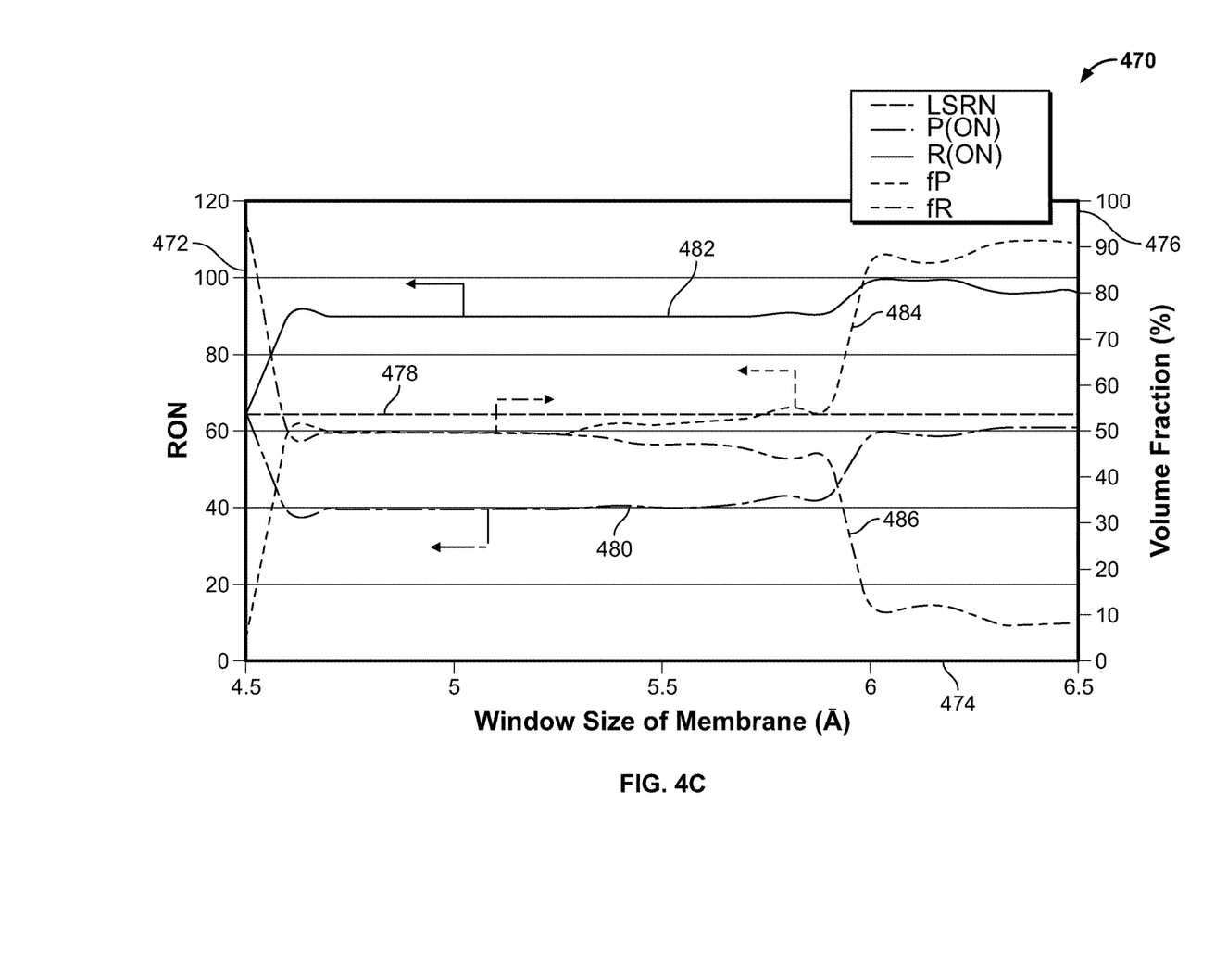

FIGS. 4A-4C are graphs 400, 440, and 470, respectively, that illustrate results of a simulation model of an on-board fuel separation system according to the present disclosure. The simulation model which results are shown in graphs 400, 440, and 470 simulates an operation of an on-board fuel separation system for a vehicle that includes molecular sieve as a membrane of a fuel separator (for example, membrane 312 of separator 310 in FIG. 3, or membrane 212 of separator 210 in FIG. 2).

FIG. 4A illustrates results of the simulation model in which an input fuel supply of gasoline at 91 RON was used (for example, as the input fuel stream 304 in FIG. 3, or as the input fuel stream 204 in FIG. 2). Graph 400 includes a y-axis 402 that represents RON, an x-axis 404 that represents a pore size of the membrane in angstroms (Å), and a y-axis 406 that represents a volume fraction (percentage) of resulting permeate and retentate fuel streams. The graph 400 shows five plots. Plot 408 represents the RON of the input fuel stream, which is constant at 91 since this simulation model uses 91 RON gasoline as the input fuel stream. Plot 410 represents RON of the separated permeate fuel stream relative to pore size of the membrane. Plot 412 represents RON of the separated retentate fuel stream relative to pore size of the membrane. Plot 414 represents the volume fraction of the permeate fuel stream relative to pore size of the membrane. Plot 416 represents the volume fraction of the retentate fuel stream relative to pore size of the membrane. As shown, the sum of the volume fractions of the permeate and retentate fuel streams is always 100% regardless of pore size of the membrane.

As illustrated, the permeate RON 410 and retentate RON 412 diverge between about 4.5 and 5.5 Å pore size of the membrane, with the permeate RON 410 dropping from 91 to about 55 and the retentate RON 412 rising from 91 to about 105. Between 5.5 and 6.5 Å pore size, the permeate RON 410 and retentate RON 412 generally converge again toward 91 RON. As further illustrated, the permeate volume fraction 414 and retentate volume fraction 416 converge between about 4.5 and 5.5 Å to steady states of about 22% and 78%, respectively. Between 5.5 and about 6 Å, the volume fractions then cross paths (for example, at less than about 6 Å) and begin to oppositely diverge, with the permeate volume fraction 414 and retentate volume fraction 416 adjusting to about 92% and 8%, respectively. As graph 400 shows, at about 6 Å pore size for 91 gasoline, a larger volume fraction of the permeate fuel stream begins to occur as more fractional components fit (for example, according to kinetic diameter, molecular weight, or other molecular dimension) through the pores of the membrane.

FIG. 4B illustrates results of the simulation model in which an input fuel supply of gasoline at 95 RON was used (for example, as the input fuel stream 304 in FIG. 3, or as the input fuel stream 204 in FIG. 2). Graph 440 includes a y-axis 442 that represents RON, an x-axis 444 that represents a pore size of the membrane in angstroms (Å), and a y-axis 446 that represents a volume fraction (percentage) of resulting permeate and retentate fuel streams. The graph 440 shows five plots. Plot 448 represents the RON of the input fuel stream, which is constant at 95 since this simulation model uses 95 RON gasoline as the input fuel stream. Plot 450 represents RON of the separated permeate fuel stream relative to pore size of the membrane. Plot 452 represents RON of the separated retentate fuel stream relative to pore size of the membrane. Plot 454 represents the volume fraction of the permeate fuel stream relative to pore size of the membrane. Plot 456 represents the volume fraction of the retentate fuel stream relative to pore size of the membrane. As shown, the sum of the volume fractions of the permeate and retentate fuel streams is always 100% regardless of pore size of the membrane.

As illustrated, the permeate RON 450 and retentate RON 452 diverge between about 4.5 and 5.5 Å pore size of the membrane, with the permeate RON 450 dropping from 95 to about 70 and the retentate RON 452 rising from 95 to about 105. Between 5.5 and 6.5 Å pore size, the permeate RON 450 and retentate RON 452 start to converge again toward 95 RON, but at the larger pore size (in other words, towards 6.5 Å), the permeate RON 450 steadies at about 115 RON while the retentate RON 452 steadies at 95 RON. As further illustrated, the permeate volume fraction 454 and retentate volume fraction 456 converge between about 4.5 and 5.5 Å to steady states of about 22% and 78%, respectively. Between 5.5 and about 6 Å, the volume fractions then cross paths (for example, at less than about 6 Å) and begin to oppositely diverge, with the permeate volume fraction 454 and retentate volume fraction 456 adjusting to about 92% and 8%, respectively. As graph 440 shows, at about 6 Å pore size for 95 gasoline, a larger volume fraction of the permeate fuel stream begins to occur as more fractional components fit (for example, according to kinetic diameter, molecular weight, or other molecular dimension) through the pores of the membrane.

FIG. 4C illustrates results of the simulation model in which an input fuel supply of LSRN (at about 65 RON) was used (for example, as the input fuel stream 304 in FIG. 3, or as the input fuel stream 204 in FIG. 2). Graph 470 includes a y-axis 472 that represents RON, an x-axis 474 that represents a pore size of the membrane in angstroms (Å), and a y-axis 476 that represents a volume fraction (percentage) of resulting permeate and retentate fuel streams. The graph 470 shows five plots. Plot 478 represents the RON of the input fuel stream, which is constant at about 65 since this simulation model uses 65 RON LSRN as the input fuel stream. Plot 480 represents RON of the separated permeate fuel stream relative to pore size of the membrane. Plot 482 represents RON of the separated retentate fuel stream relative to pore size of the membrane. Plot 484 represents the volume fraction of the permeate fuel stream relative to pore size of the membrane. Plot 486 represents the volume fraction of the retentate fuel stream relative to pore size of the membrane. As shown, the sum of the volume fractions of the permeate and retentate fuel streams is always 100% regardless of pore size of the membrane.

As illustrated, the permeate RON 480 and retentate RON 482 diverge between about 4.5 and 6 Å pore size of the membrane, with the permeate RON 480 dropping from about 65 to about 40 and the retentate RON 482 rising from 65 to about 90; these values hold fairly steady between about 4.5 and 5.5 Å. Between 6 and 6.5 Å pore size, the permeate RON 480 rises to about 60 while the retentate RON 482 rises to about 100 RON. As further illustrated, the permeate volume fraction 484 and retentate volume fraction 486 converge between about 4.5 and almost 5.5 Å to steady states of about 50% each. Between almost 5.5 and about 6 Å, the volume fractions then cross paths (for example, at less than about 5.5 Å) and begin to oppositely diverge, with the permeate volume fraction 484 and retentate volume fraction 486 adjusting to about 55% and 45%, respectively. The permeate volume fraction 484 and retentate volume fraction 486 diverge sharply at about 6 Å, with the permeate volume fraction 484 rising to about 90% and the retentate volume fraction 486 decreasing to about 10%. As graph 470 shows, at about 6 Å pore size for LSRN, a larger volume fraction of the permeate fuel stream begins to occur as more fractional components fit (for example, according to kinetic diameter, molecular weight, or other molecular dimension) through the pores of the membrane.

Figure 5:
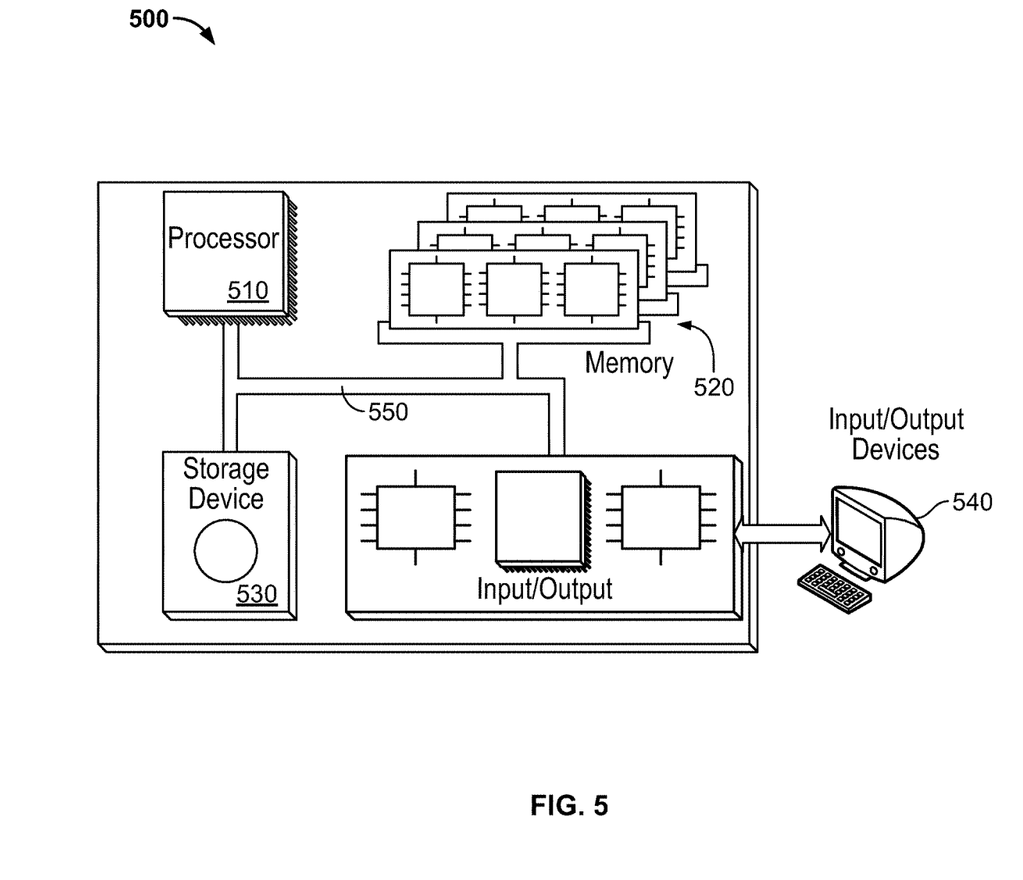
FIG. 5 is a schematic illustration of an example controller for an on-board fuel separation system according to the present disclosure.

FIG. 5 is a schematic illustration of an example controller 500 (or control system) for an on-board fuel separation system. For example, the controller 500 can be used for the operations described previously, for example as or as part of the control systems 218 or 330, or other controllers described herein. For example, the controller 500 may be communicably coupled with, or as a part of, one or both of a vehicle engine and on-board fuel separation system as described herein.

The controller 500 is intended to include various forms of digital computers, such as printed circuit boards (PCB), processors, digital circuitry, or otherwise that is part of a vehicle. Additionally the system can include portable storage media, such as, Universal Serial Bus (USB) flash drives. For example, the USB flash drives may store operating systems and other applications. The USB flash drives can include input/output components, such as a wireless transmitter or USB connector that may be inserted into a USB port of another computing device.

The controller 500 includes a processor 510, a memory 520, a storage device 530, and an input/output device 540. Each of the components 510, 520, 530, and 540 are interconnected using a system bus 550. The processor 510 is capable of processing instructions for execution within the controller 500. The processor may be designed using any of a number of architectures. For example, the processor 510 may be a CISC (Complex Instruction Set Computers) processor, a RISC (Reduced Instruction Set Computer) processor, or a MISC (Minimal Instruction Set Computer) processor.

In one implementation, the processor 510 is a single-threaded processor. In another implementation, the processor 510 is a multi-threaded processor. The processor 510 is capable of processing instructions stored in the memory 520 or on the storage device 530 to display graphical information for a user interface on the input/output device 540.

The memory 520 stores information within the controller 500. In one implementation, the memory 520 is a computer-readable medium. In one implementation, the memory 520 is a volatile memory unit. In another implementation, the memory 520 is a non-volatile memory unit.

The storage device 530 is capable of providing mass storage for the controller 500. In one implementation, the storage device 530 is a computer-readable medium. In various different implementations, the storage device 530 may be a floppy disk device, a hard disk device, an optical disk device, or a tape device.

The input/output device 540 provides input/output operations for the controller 500. In one implementation, the input/output device 540 includes a keyboard and/or pointing device. In another implementation, the input/output device 540 includes a display unit for displaying graphical user interfaces.

The features described can be implemented in digital electronic circuitry, or in computer hardware, firmware, software, or in combinations of them. The apparatus can be implemented in a computer program product tangibly embodied in an information carrier, for example, in a machine-readable storage device for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer. Additionally, such activities can be implemented via touchscreen flat-panel displays and other appropriate mechanisms.

The features can be implemented in a control system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include a local area network ("LAN"), a wide area network ("WAN"), peer-to-peer networks (having ad-hoc or static members), grid computing infrastructures, and the Internet.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

A number of implementations have been described. Nevertheless, it will be understood that various modifications may be made without departing from the spirit and scope of the disclosure. For example, example operations, methods, or processes described herein may include more steps or fewer steps than those described. Further, the steps in such example operations, methods, or processes may be performed in different successions than that described or illustrated in the figures. Accordingly, other implementations are within the scope of the following claims.

What is claimed is:

1. A method for separating a fuel on-board a vehicle, comprising:
   circulating an input fuel stream from a supply fuel tank to a first heat exchanger fluidly coupled between the supply fuel tank and an on-board fuel separator;
   circulating a first fractional fuel stream directly from the on-board fuel separator to the first heat exchanger;
   heating the input fuel stream in the first heat exchanger with heat transferred from the first fractional fuel stream;

circulating the heated input fuel stream from the first heat exchanger to a second heat exchanger fluidly coupled in series between the first heat exchanger and the on-board fuel separator;

circulating a second fractional fuel stream directly from the on-board fuel separator to the second heat exchanger;

further heating the input fuel stream in the second heat exchanger with heat transferred from the second fractional fuel stream;

circulating the further heated input fuel stream to the on-board fuel separator;

separating the further heated input fuel stream into the first fractional fuel stream and the second fractional fuel stream, the on-board fuel separator comprising a membrane that comprises a plurality of pores sized based on a molecular size of one or more components of the first fractional fuel stream, the membrane comprising a molecular sieve or nanofilter;

passing the first fractional fuel stream through the membrane; and circulating the first and second fractional fuel streams to respective first and second fractional fuel tanks, the first fractional fuel stream defined by a first auto-ignition characteristic value, and the second fractional fuel stream defined by a second auto-ignition characteristic value that is different than the first auto-ignition characteristic value.

2. The method of claim 1, further comprising:
reducing, based on the transferred heat, a temperature of at least one of the first or second fractional fuel stream from at or near a vapor phase temperature to at or near a liquid phase temperature.

3. The method of claim 1, wherein heating the input fuel stream in the heat exchanger comprises heating the input fuel stream from a liquid phase temperature to at or near a vapor phase temperature.

4. The method of claim 3, further comprising:
circulating the further heated input fuel stream to a heater fluidly coupled between the second heat exchanger and the on-board fuel separator; and
further heating the further heated input fuel stream, with the heater, to at least the vapor phase temperature.

5. The method of claim 1, wherein the first fractional fuel stream comprises at least one of linear or mono-branch paraffins, and the second fractional fuel stream comprises at least one of multi-branched paraffins, naphenes, aromatics, olefins, or oxygenates.

6. The method of claim 1, wherein the first auto-ignition characteristic value comprises a first research octane number (RON) or a first cetane number, and the second auto-ignition characteristic value comprises a second RON or a second cetane number.

7. The method of claim 6, wherein the first RON or cetane number is less than a RON or cetane number of the input fuel stream, and the second RON or cetane number is greater than the RON or cetane number of the input fuel stream.

8. The method of claim 1, wherein the molecular size comprises a molecular diameter.

9. An on-board fuel separation system, comprising:
a supply fuel tank configured to store an input fuel stream;
a first heat exchanger fluidly coupled to the supply fuel tank and configured to receive the input fuel stream from the supply fuel tank and heat the input fuel stream to deliver to a fuel separator, the first heat exchanger fluidly coupled to the fuel separator to receive a first fractional fuel stream from the fuel separator to transfer heat, in the first heat exchanger, from the first fractional fuel stream to the input fuel stream;

a second heat exchanger fluidly coupled in series between the first heat exchanger and the fuel separator and configured to receive the input fuel stream from the first heat exchanger and further heat the input fuel stream to deliver to the fuel separator, the second heat exchanger fluidly coupled to the fuel separator to receive a second fractional fuel stream from the fuel separator to transfer heat, in the second heat exchanger, from the second fractional fuel stream to the input fuel stream;

the fuel separator fluidly coupled to the second heat exchanger and configured to separate the input fuel stream into the first fractional fuel stream and a second fractional fuel stream, the fuel separator comprising a membrane that comprises a plurality of pores sized based on a molecular size of one or more components of the first fractional fuel stream, the membrane comprising a molecular sieve or nanofilter;

a first fractional fuel tank fluidly coupled to the fuel separator to receive the first fractional fuel stream passed through the membrane, the first fractional fuel stream defined by a first auto-ignition characteristic value; and a second fractional fuel tank coupled to the fuel separator to receive the second fractional fuel stream from the fuel separator, the second fractional fuel stream defined by a second auto-ignition characteristic value that is different than the first auto-ignition characteristic value.

10. The on-board fuel separation system of claim 9, wherein a temperature of the at least one first or second fractional fuel stream is adjustable, in the respective first or second heat exchangers, from at or near a vapor phase temperature to at or near a liquid phase temperature.

11. The on-board fuel separation system of claim 9, wherein at least one of the first heat exchanger or the second heat exchanger is configured to heat the input fuel stream from a liquid phase temperature to at or near a vapor phase temperature.

12. The on-board fuel separation system of claim 11, further comprising:
a heater coupled between the second heat exchanger and the fuel separator and configured to further heat the heated input fuel stream to at least the vapor phase temperature.

13. The on-board fuel separation system of claim 9, wherein the first fractional fuel stream comprises at least one of linear or mono-branch paraffins, and the second fractional fuel stream comprises at least one of multi-branched paraffins, naphenes, aromatics, olefins, or oxygenates.

14. The on-board fuel separation system of claim 9, wherein the first auto-ignition characteristic value comprises a first research octane number (RON) or a first cetane number, and the second auto-ignition characteristic value comprises a second RON or a second cetane number, and the first RON or cetane number is less than a RON or cetane number of the input fuel stream, and the second RON or cetane number is greater than the RON or cetane number of the input fuel stream.

15. The on-board fuel separation system of claim 9, wherein the molecular size comprises a molecular diameter.

16. A vehicle system, comprising
a vehicle;
a fuel-powered internal combustion engine mounted in the vehicle;
a supply fuel tank;
an on-board fuel separation system comprising:

a first heat exchanger fluidly coupled to the supply fuel tank and configured to receive an input fuel stream from the supply fuel tank and heat the input fuel stream to deliver to a fuel separator, the first heat exchanger fluidly coupled to the fuel separator to receive a first fractional fuel stream from the fuel separator to transfer heat, in the first heat exchanger, from the first fractional fuel stream to the input fuel stream;

a second heat exchanger fluidly coupled in series between the first heat exchanger and the fuel separator and configured to receive the input fuel stream from the first heat exchanger and further heat the input fuel stream to deliver to the fuel separator, the second heat exchanger fluidly coupled to the fuel separator to receive a second fractional fuel stream from the fuel separator to transfer heat, in the second heat exchanger, from the second fractional fuel stream to the input fuel stream; and the fuel separator fluidly coupled to the second heat exchanger and configured to separate the input fuel stream into the first fractional fuel stream and the second fractional fuel stream, the fuel separator comprising a membrane that comprises a plurality of pores sized based on a molecular diameter of one or more components of the first fractional fuel stream, the membrane comprising a molecular sieve or nanofilter;

a first fuel tank fluidly coupled to the fuel separator to receive the first fractional fuel stream passed through the membrane, the first fractional fuel stream defined by a first auto-ignition characteristic value; and a second fuel tank coupled to the fuel separator to receive the second fractional fuel stream from the fuel separator, the second fractional fuel stream defined by a second auto-ignition characteristic value that is different than the first auto-ignition characteristic value.

17. The vehicle system of claim 16, wherein a temperature of the first fractional fuel stream is adjustable, in the first heat exchanger, from at or near a vapor phase temperature to at or near a liquid phase temperature.

18. The vehicle system of claim 16, wherein at least one of the first heat exchanger or the second heat exchanger is configured to heat the input fuel stream from a liquid phase temperature to at or near a vapor phase temperature.

19. The vehicle system of claim 16, wherein the first fractional fuel stream comprises at least one of linear or mono-branch paraffins, and the second fractional fuel stream comprises at least one of multi-branched paraffins, naphenes, aromatics, olefins, or oxygenates.

20. The vehicle system of claim 16, wherein the first auto-ignition characteristic value comprises a first research octane number (RON) or a first cetane number, and the second auto-ignition characteristic value comprises a second RON or a second cetane number, and first RON or cetane number is less than a RON or cetane number of the input fuel stream, and the second RON or cetane number is greater than the RON or cetane number of the input fuel stream.

21. The vehicle system of claim 16, wherein the on-board fuel separation system further comprises a heater coupled between the second heat exchanger and the fuel separator and configured to further heat the heated input fuel stream to at least the vapor phase temperature.

22. The vehicle system of claim 16, wherein a temperature of the second fractional fuel stream is adjustable, in the second heat exchanger, from at or near a vapor phase temperature to at or near a liquid phase temperature.

23. The method of claim 1, further comprising:
directly circulating the first fractional fuel stream from the on-board fuel separator to the first heat exchanger at a constant temperature in vapor phase; and
directly circulating the second fractional fuel stream from the on-board fuel separator to the second heat exchanger at a constant temperature in vapor phase.

* * * * *